United States Patent [19]

Lo et al.

[11] Patent Number: 4,876,039

[45] Date of Patent: Oct. 24, 1989

[54] PROCESS FOR PREPARING SILICONE MICROPARTICLES CURED BY A MICHAEL ADDITION REACTION

[75] Inventors: Peter Y. K. Lo; Maris J. Ziemelis, both of Midland, Mich.

[73] Assignee: Dow Corning Corporation, Midland, Mich.

[21] Appl. No.: 195,928

[22] Filed: May 19, 1988

Related U.S. Application Data

[63] Continuation of Ser. No. 926,763, Nov. 4, 1986, abandoned.

[51] Int. Cl.$^4$ .......................... A61K 9/58; B01J 13/02; C08G 77/26
[52] U.S. Cl. ..................................... 264/4.7; 71/64.11; 71/DIG. 1; 252/389.5; 264/4.3; 424/462; 424/497; 427/213.33; 427/213.34; 512/4; 514/963; 528/32; 528/33
[58] Field of Search ..................... 427/213.34; 264/4.7; 424/462, 497; 528/32, 33; 512/4; 514/963

[56] References Cited

U.S. PATENT DOCUMENTS

| | | | |
|---|---|---|---|
| 3,033,815 | 5/1962 | Pike | 528/38 |
| 3,975,251 | 8/1976 | McGinniss | 204/181.7 |
| 4,122,074 | 10/1978 | Pepe et al. | 526/26 |
| 4,198,331 | 4/1980 | Buchwalter et al. | 523/411 |
| 4,209,455 | 6/1980 | Pepe | 556/419 |
| 4,293,397 | 10/1981 | Sato et al. | 528/33 X |
| 4,293,677 | 10/1981 | Imai | 528/31 X |
| 4,370,160 | 1/1983 | Ziemelis | 71/117 |
| 4,429,082 | 1/1984 | Lee et al. | 525/426 |
| 4,604,444 | 8/1986 | Donnadieu et al. | 528/17 X |

Primary Examiner—Richard D. Lovering
Attorney, Agent, or Firm—Alexander Weitz

[57] ABSTRACT

Microparticles, such as microspheres and microcapsules, comprising a solid organopolysiloxane are prepared by curing a dispersion of discrete entities by means of a Michael-type addition reaction. The discrete entities are dispersed in a fluid continuous phase and are sphere-like particles of a curable liquid organopolysiloxane composition, or such a liquid organopolysiloxane composition containing a material to be encapsulated. The microparticles may be elastomeric or resinous and are useful as filler particles and time-release capsules.

31 Claims, No Drawings

PROCESS FOR PREPARING SILICONE MICROPARTICLES CURED BY A MICHAEL ADDITION REACTION

This is a continuation of copending application Ser. No. 926,763, filed on Nov. 4, 1986, now abandoned.

BACKGROUND OF THE INVENTION

This invention relates to a process for preparing microparticles comprising a solid organopolysiloxane. More particularly, this invention relates to the preparation of microspheres and microcapsules using a two-part siloxane composition wherein one siloxane polymer contains amine functionality and is capable of reacting with the other siloxane polymer, which contains acryloxy, methacryloxy or acrylamide functionality (hereinafter acryl-functional siloxane). The reaction, which leads to a cured elastomer or resin, takes place via a Michael-type addition between the amine-functional siloxane and the acryl-functional siloxane.

The reaction between amine-functional and alpha-beta olefinically unsaturated compounds is well known in the art and is often referred to as a Michael addition. Pike et al., in U.S. Pat. No. 3,033,815, disclose the preparation of organosilicon compounds containing a substituted amino group attached to at least one silicon atom thereof through an alkylene linkage of at least three carbon atoms. This is accomplished by reacting an aminoalkyl silicon compound with a variety of alpha-beta olefinically unsaturated organic compounds. The reactive aminoalkylene group can be attached to a silane or siloxane structure. The compounds taught by Pike et al. are said to find use as sizes for fibrous materials, modifiers for polydimethylsiloxane oils and gums, adhesives and flocculation agents.

In Pepe et al., U.S. Pat. No. 4,122,074 polyester aminoalkylalkoxysilanes are provided by effecting the Michael addition reaction of an unsaturated conjugated polyester with an aminoalkylalkoxysilane. These polymers are said to have utility as adhesion promoters between siliceous materials and organic resins and can further act as a size, or protective coating, when the siliceous material is glass cloth or fiber.

Pepe U.S. Pat. No. 4,209,455, discloses aminoorganosilicon acylamino compounds which are prepared by a Michael addition of an amino-functional alkoxysilane to an olefinic carboxylate ester to form the corresponding amino-carboxylic acid ester of the silane. This amino-carboxylic acid ester-silane is then amidated with either a primary amino silicon compound or a primary organoamine to produce the desired aminoorganosilicon acylamino compound. Alkoxy groups on the silicon of these final compounds may be hydrolyzed and condensed, with or without other conventional organosilanes, to form polymeric siloxanes having the respective amine functionality attached thereto. The silanes and siloxane compositions thus produced are said to be useful as sizes for fibrous materials (i.e., as coupling agents) and as additives for hydroxyl containing organic thermoplastic polymer compositions.

Lee U.S. Pat. No. 4,429,082, disclose film-forming resins produced by the Michael addition of an amine-functional silane or amine-functional siloxane to a condensation product which contains at least 2 amine reactive acrylyl residues per molecule. Examples of useful condensation products (backbone polymer) include unsaturated polyester polyol polyacrylate, alkydpolyol polyacrylate and polyurethanepolyol polyacrylate. The silanes employed in the Michael addition contain alkoxy groups which are retained after the addition and allow the products of this invention to be cured with the aid of organometallic catalysts. The resins so produced are said to be useful film-forming components in coating compositions which can be cured at low temperatures and preferably include a low organic solvent content.

Acryl-functional silicone compounds are disclosed by Lee and Lutz in copending application Ser. No. 816,477, filed Jan. 6, 1986 now U.S. Pat. No. 4,697,026, and assigned to the assignee of this invention. In this case, acryl silane (or silicone) compounds are made by reacting an amine-functional silane (or amine-functional silicone) with a di- or multi-functional acryl compound by a Michael addition reaction. These acryl silane (silicone) compounds are said to be purer than those formed by other routes since no catalyst is used and no by-products are formed. The compounds are further said to have utility as adhesion promoters (silanes) and as coatings compositions which can be cured by ultraviolet radiation (silicones).

The Michael addition reaction has also been employed in the heat cure of electrocoating compositions. McGinniss, in U.S. Pat. No. 3,975,251, teaches coating a cathode substrate with a polymer having pendant amine groups and a cross-linking agent having alpha-beta-ethylenically unsaturated carbonyl groups. The coating process employs an aqueous dispersion of the polymer and cross-linking agent wherein the amine groups are first protonated with an acid to render the polymer dispersible prior to electrodeposition. Upon electrodeposition, the amine groups become deprotonated and then cross-link with the alpha-beta-ethylenically unsaturated carbonyls upon heating to form a fully cured coating on the substrate.

Buchwalter et al., in U.S. Pat. No. 4,198,331, teach a curable resinous composition comprising a polyamine resin containing amino groups, which are stable under the curing conditions, and a Michael adduct of an organic material containing alpha, beta-ethylenically unsaturated moieties in conjugation with carbonyl moieties reacted with amines, which is unstable under curing conditions. When these compositions are heated to curing temperatures, it is believed the adduct decomposes releasing amine which volatilizes, generating alpha, beta-ethylenically unsaturated carbonyls which cure via a Michael addition reaction with non-volatile amines present in the composition.

The use of silicones in the preparation of microcapsules is known in the art. Ziemelis, in U.S. Pat. No. 4,370,160, hereby incorporated by reference, teaches a process for preparing microspheres of solid organopolysiloxane or microcapsules which consist essentially of an internal material dispersed throughout a solid organopolysiloxane. In brief, this process comprises irradiating a dispersion of discrete entities with ultraviolet light. The discrete entities are dispersed in a UV-transparent fluid continuous phase and are sphere-like particles of a UV-curable, liquid organopolysiloxane composition which is immiscible with the continuous phase, or such a liquid organopolysiloxane composition containing a material to be encapsulated. The microparticles may be elatomeric or resinous and are useful as filler particles and time-release capsules. The liquid organopolysiloxane composition, in turn, consists essentially of a mixture of an organopolysiloxane having at least two vinyl (or butenylene) radicals per molecule and an organopolysiloxane having at least two mercaptoalkyl (or silicon-bonded hydrogen) radicals per molecule.

The process taught by Ziemelis, although quite useful for UV-transparent materials, can find little utility when the continuous phase itself is UV-opaque. In such an instance, irradiation would be ineffective, save in very thin sections. Furthermore, should the material to be encapsulated contain any component which can "poison" or retard the UV-care, this process would again be of little value.

These references do not suggest the use of the Michael addition reaction as a method for cross-linking silicone polymers and copolymers, particularly as applied to the formation of silicone microshperes and microcapsules as described in the instant invention.

SUMMARY OF THE INVENTION

It has now been found that certain amine-functional organopolysiloxanes may be combined with acryloxy, methacryloxy or acrylamide functional organopolysiloxanes to form a composition which may be readily dispersed in an opaque or clear continuous fluid phase using conventional surfactants. Upon reaction of the amine and acryl functionalities, without benefit of a catalyst, these compositions cure, preferably at room temperature, to the solid microspheres or microcapsules.

The present invention therefore relates to a process for preparing microspheres of solid organopolysiloxane, said process comprising:

(I) preparing a dispersion of discrete entities in a fluid continuous phase by dispersing, in the continuous phase fluid, a liquid organopolysiloxane composition convertible to the solid state at room temperature, said liquid organopolysiloxane composition being insoluble in the fluid continuous phase and consisting essentially of
  (i) an organopolysiloxane having attached thereto through silicon-carbon bonds an average of at least two X groups per molecule, wherein X is a monovalent organic moiety containing at least one —NHR" radical, wherein R" is selected from hydrogen or alkyl having 3 to 6 carbon atoms, and
  (ii) an organopolysiloxane having attached thereto through silicon-carbon bonds an average of at least two Z groups per molecule, wherein Z is a monovalent organic moiety containing at least one acryl-funtional radical which is capable of reacting with said —NHR" radical, said acryl-functional radical being selected from acryloxy, methacryloxy or acrylamide radicals, at least one of (i) and (ii) having an average of more than two of said X groups and said Z groups, respectiviely, per molecule; and (II) curing said composition until said organopolysiloxane composition is converted to the solid state.

This invention further relates to a process for preparing microcapsules of an internal material localized as a core in a solid organopolysiloxane, said process comprising:

(I) preparing a dispersion of discrete entities in a fluid continuous phase by dispersing the internal material in the continuous phase fluid and simultaneously or subsequently codispersing therewith a liquid organopolysiloxane composition convertible to the solid state at room temperature and insoluble in the fluid continuous phase, said composition consisting essentially of the above-described components (i) and (ii); and (II) curing said composition until said organopolysiloxane composition is converted to the solid state.

This invention further relates to a process for preparing microcapsules of an internal material dispersed throughout a solid organopolysiloxane, said process comprising:

(I) preparing a dispersion of discrete entities in a fluid continuous phase by dispersing or dissolving the internal material in a liquid organopolysiloxane composition convertible to the solid state at room temperature, and dispersing the resulting dispersion or solution in the continuous phase fluid, said organopolysiloxane composition being insoluble in the fluid continuous phase and consisting essentially of the above-described components (i) and (ii); and (II) curing said composition until said organopolysiloxane composition is converted to the solid state.

DETAILED DESCRIPTION OF THE INVENTION

Microparticles, as used herein, is a generic term and includes microspheres and microcapsules comprising a solid organopolysiloxane. Microspheres, as used herein, are homogeneous microparticles consisting essentially of solid organopolysiloxane. Microcapsules, as used herein, are homogeneous or heterogeneous microparticles consisting essentially of an internal material which is different from and surrounded by the solid organopolysiloxane. Microcapsules may contain the internal (i.e., encapsulated) material dispersed throughout, or localized as a core in, the solid organopolysiloxane.

Microparticles, for the purposes of this invention, are essentially sphere-like particles having a diameter of up to about 5 mm, but preferably from 0.005 to 1 mm. Microcapsules having a relatively large solid core may deviate from a sphere-like shape to the extent that the shape of the solid core deviates from a sphere-like shape. It is to be understood that the method of this invention provides predominantly discrete microparticles; however, small amounts of aggregated microparticles, held together by physical and/or chemical bonding may be prepared thereby. Liquid organopolysiloxane compositions convertible to the solid state which are suitable in the process of this invention must experience a change to the solid, i.e., non-flowing, state when cured via a Michael addition reaction. Compositions meeting this requirement comprise a liquid homogeneous mixture of two types of organopolysiloxanes: (i) an organopolysiloxane bearing an average of at least two reactive amine radicals per molecule and (ii) an organopolysiloxane bearing an average of at least two reactive acryl radicals per molecule. The term "acryl" as used herein denotes a generic representation of acryloxy, methacryloxy or acrylamide functionalities. Furthermore, at least one of said organopolysiloxanes has an average of more than two, preferably three or more, of said reactive radicals per molecule. Preferably, both component (i) and component (ii) have an average of three or more of said reactive amine and reactive acryl radicals, respectively, per molecule. Such curable compositions are disclosed in copending application to the instant inventors entitled "Curable Organopolysiloxane Composition," Ser. No. 962,762, filed Nov. 4, 1986 now U.S. Pat. No. 4,698,406, and assigned to the assignee of this invention.

Organopolysiloxane (i) of the present invention is an amine-functional organopolysiloxane which consists of a plurality of organosiloxane units of the general formula $$R_a SiO_{(4-a-b)/2} \atop X_b \qquad (I)$$

wherein X is a reactive amine-functional organic group bearing at least one —NHR'' group, in which R'' is hydrogen or an alkyl radical having 1–6 carbon atoms. On average, at least two reactive X groups per molecule of organopolysiloxane (i) are required to be within the scope of the present invention.

In the above formula, R is a non-reactive group which may be independently selected from alkyl radicals having 1–6 carbon atoms, such as methyl, ethyl, propyl, butyl, isopropyl or hexyl. The R group may also be selected from cycloaliphatic radicals, such as cyclopentyl, cyclohexyl and cyclooctyl radicals. Alternatively, R can be an aryl group such as phenyl, benzyl, styryl, tolyl and xenyl. Still further, R may be a monovalent halohydrocarbyl group having 1 to 6 carbon atoms such as 3,3,3-trifluoropropyl, 3-chloropropyl and perfluorobutylethyl. Finally, R may be a haloaromatic group, such as 2,3-dichlorophenyl. It is preferred that R is selected from methyl, phenyl or 3,3,3-trifluoropropyl radicals. In any given organosiloxane unit of component (i), the value of a may be 0, 1, 2 or 3, the value of b may be 0, 1 or 2 and the sum (a+b) is less than 4.

The exact nature of the organic portion of the X group is not critical to the operability of this invention, but said organic portion must exclude functionality which would react with the —NHR'' groups thereon. Preferably, the organic portion of X should also not react with the acryl-functional groups of component (ii), described infra. The organic portion must further not react with said continuous phase. In other words, the organic portion of the X groups serves only as a structure to link the amine functionality thereof with the main body of organopolysiloxane (i) and is preferably chemically inert. Thus, for example, the organic portion of Z may be a divalent connecting group such as a hydrocarbon having at least 3 carbon atoms or an arylene group, such as phenylene.

In a preferred embodiment of this invention, the X group is —R'(NHCH$_2$CH$_2$)$_g$NR''H. In this embodiment, R' is a divalent hydrocarbyl group having from 3 to 6 carbon atoms such as trimethylene, tetramethylene and isobutylene. Preferably, R' is trimethylene or isobutylene. R'' is hydrogen or an alkyl radical having from 1 to 6 carbon atoms, preferably hydrogen, and g is an integer having a value between zero and 4. Preferably g is one.

It is further preferred that the amine-functional organopolysiloxane (i) be a linear copolymer selected from structures which may be represented by the average formulae $$R_3SiO(R_2SiO)_x(RSiO)_y SiR_3 \atop X \qquad (II)$$

or $$R_2SiO(R_2SiO)_x SiR_2 \atop X \qquad X \qquad (III)$$

wherein the R groups are independently selected from the nonreactive species enumerated above, the average value of x may vary from zero to about 900 and the average value of y may vary from 2 to about 100. It is also preferred that the R groups are methyl radicals and X is —R'(NHCH$_2$CH$_2$)$_g$NR''H, as defined above. In these embodiments, particularly preferred X groups are

—CH$_2$CH$_2$CH$_2$NCH$_2$CH$_2$NH$_2$
  |
  H

—CH$_2$CH$_2$CH$_2$NH$_2$
—CH$_2$CH$_2$CH$_2$NH(CH$_3$)
and

—CH$_2$CHCH$_2$NH(CH$_3$)
  |
  CH$_3$ while the most preferred X group is X', which may be represented by the formula —CH$_2$CHCH$_2$NCH$_2$CH$_2$NH$_2$.    (Group X')
  |      |
  CH$_3$   H The most preferred amine-functional organopolysiloxanes have the structure $$Me_3SiO(Me_2SiO)_x(MeSiO)_y SiMe_3 \atop X' \qquad (IV)$$

wherein X' has been defined and Me hereinafter denotes the methyl radical. In this case, x represents the average number of dimethyl units and can range from zero to 900, preferably from 50 to 400. Likewise, y represents the average number of methyl-aminofunctional units and can range from 2 to about 100, preferably from 2 to 30. These amine-functional siloxanes are fluids having a viscosity between about 50 and 2000 cP at 25° C.

The amine-functional organopolysiloxanes of this invention are well known in the art and some of them are available commercially. There is thus no need for a detailed description as to their preparation herein.

Component (ii) of the present invention is an acryl-functional organopolysiloxane consisting of a plurality of units of the general formula $$R_c SiO_{(4-c-d)/2} \atop Z_d \qquad (V)$$

wherein Z is a reactive acryl-functional organic group bearing at least one group selected from acryloxy, methacryloxy or acrylamide radicals and R is the nonreactive group defined above. On average, at least two reactive Z groups per molecule of organopolysiloxane (ii) are required to be within the scope of the present invention. In any given organosiloxane unit of component (ii), the value of c may be 0, 1, 2 or 3, the value of d may be 0, 1 or 2 and the sum (c+d) is less than 4.

As in the case of component (i) the exact nature of the organic portion of the Z group is not critical to the operability of this invention, but said organic portion must exclude functionality which would react with the continuous fluid phase or the acryl functionality thereon. Preferably, the organic portion of Z should also not react with the amine-functional groups of component (i), described supra. In other words, the organic portion of the Z groups again serves only as a structure to link the acryl functionality thereof with the main body of organopolysiloxane (ii) and is preferably chemically inert. In this regard, the term "inert" defines structures which will not interfere with the reaction between the amine and acryl functionalities of components (i) and (iie, respectively. Thus, for example, the organic portion of z may be a divalent connecting groups such as a hydrocarbon having at least 3 carbon atoms or an arylene group, such as phenylene.

The acryl-functional siloxanes employed in the present invention are well known in the art and have been synthesized by various procedures. For example, acryl-functional siloxane copolymers suitable for use in the present invention may contain the Z group

—R'''OA wherein R''' is a divalent hydrocarbon radical having 1 to 18 carbon atoms, or the corresponding oxyalkylene radical, and A is the radical $$CH_2=C(B)C=O$$
| in which B is hydrogen or methyl. Such copolymers may be prepared by methods described in Tolentino U.S. Pat. No. 4,568,566, hereby incorporated by reference.

Another example of an acryl-functional siloxane copolymer suitable for use in the present invention contains the Z group —R'(NC$_2$H$_4$)$_k$N(CH$_2$CH(CH$_2$)$_m$OA)$_2$
    H                    OH wherein R' is a divalent hydrocarbon group, m is an integer between 1 and 10, k is 0, 1, 2, 3, or 4 and A has its previous meaning. Such copolymers may be prepared by methods described in Sato et al., U.S. Pat. No. 4,293,394 hereby incorporated by reference. Briefly, these copolymers may be prepared by the addition of a glycidyl methacrylate to an amino-terminated diorganopolysiloxane.

Another example of an acryl-functional siloxane copolymer suitable for use in the present invention contains an acrylated urethane silicone having a Z group selected from —DNHG and —DNGDNHG wherein D is a divalent saturated hydrocarbon radical of from 1 to 6 carbon atoms and G is the radical —CONHC$_{m'}$H$_{2m'}$OCOC=CH$_2$
                                   |
                                   B In the above structure, B is selected from hydrogen or the methyl radical while m' can be 2, 3 or 4. The preparation of these acryl-functional siloxanes is described by Gornowicz et al. in U.S. Pat. No. 4,563,539, hereby incorporated by reference.

Yet another example of an acryl-functional siloxane copolymer suitable for use in the present invention contains the Z group taught in Carter et al., U.S. Pat. No. 4,369,300 hereby incorporated by reference, which discloses the reaction of a silicone carbinol, a polyisocyanate and a hydroxyacrylate.

Further examples of acryl-functional siloxane copolymers suitable for use in the present invention may be made by reacting an amine-functional silicone with a di- or multi-functional acryl-functional compound by a Michael-type addition reaction. These acrylo-functional silicone compounds, and their preparation, are described in a copending application to Lee and Lutz, entitled "Acryl Functional Silicone Compounds," Ser. No. 816,477, filed Jan. 6, 1986 now U.S. Pat. No. 4,697,026, and assigned to the assignee of this invention, hereby incorporated by reference.

Acrylamide-functional organopolysiloxanes suitable for use in the present invention contain groups having the structure

—NR''''
|
CH$_2$=C(B)C=O wherein B is either hydrogen or methyl and R'''' represents hydrogen or a monovalent hydrocarbon radical. Examples of such acrylamide-functional organopolysiloxanes may be found in Varaprath U.S. Pat. No. 4,608,270, hereby incorporated by reference. In this case, the Z group has the structure

—QNAQ'NAR'''' wherein Q and Q' denote divalent hydrocarbon radicals. In the above formula, A again denotes the radical $$CH_2=C(B)C=O \qquad \text{(Group A)}$$
| wherein B is hydrogen or methyl. Briefly, such siloxanes can be prepared by mixing an acyl halide with an aminosilicon compound having at least one silicon-bonded amino-substituted hydrocarbon radical containing at least one nitrogen-bonded hydrogen. The mixing step is carried out in the presence of an aqueous solution of an alkaline material and a waterinsoluble solvent for said aminosilicon compound.

These and other acryl-functional organopolysiloxanes known in the art may be employed as component (ii) of this invention, provided they comply with the above-mentioned restrictions on reactivity.

Preferred acryl-functional organopolysiloxanes of this invention are slected from linear copolymers having structures which may be represented by the average formulae $$R_2SiO(R_2SiO)_{x'}SiR_2 \qquad \text{(VI)}$$
|                              |
Z                              Z or -continued

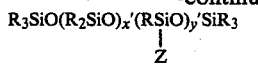 (VII)

wherein R is independently selected from the non-reactive radicals defined above, the average value of x' may vary from about 5 to about 150 and the average value of y' may vary from 2 to about 30. In formula (VI) the acryl-functional groups are terminal to the siloxane chain and in formula (VII) they are pendant to the chain.

For the purposes of the present invention, a preferred Z group is Z' which is represented by the formula

 (Group Z')

wherein R''''' is a divalent hydrocarbon group having from 3 to 6 carbon atoms. Preferably, R''''' is trimethylene. In the above formula, A has been previously defined.

Siloxanes bearing the group Z' may be prepared according to the following synthesis steps. The synthesis is illustrated for the case of siloxanes having terminal acryl- functional groups and R''''' being trimethylene, but the procedure applies equally to siloxanes having different R''''' and pendant reactive groups.

 (1)

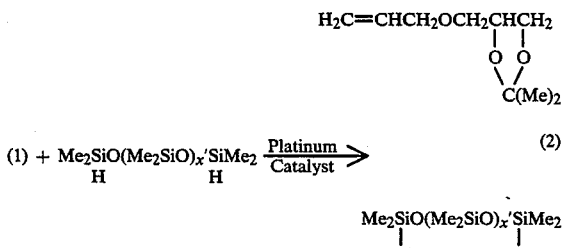

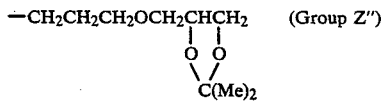 (2)

wherein Z'' denotes

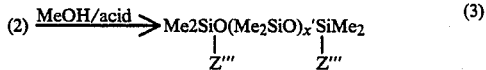 (Group Z'')

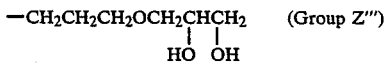 (3)

wherein Z''' denotes

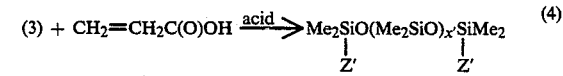 (Group Z''')

(3) + CH$_2$=CH$_2$C(O)OH $\xrightarrow{acid}$ Me$_2$SiO(Me$_2$SiO)$_x$'SiMe$_2$ (4)
                                              |                    |
                                              Z'                   Z'

This preparation has been described in detail in a copending application by P. Lo, entitled "Dioxolane, Diol and Diacrylate Silicon Compounds and Method for Their Preparation and Use," Ser. No. 914,899, filed on Oct. 3, 1986 and now abandoned, and assigned to the assignee of this invention.

Furthermore, the siloxane represented by formula (3), above, is known in the art and may alternatively be prepared by a method disclosed by Okazaki et al. in U.S. Pat. No. 4,431,789.

The most preferred acryloxy-functional organopolysiloxanes of this invention have the structure

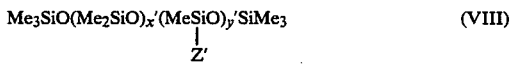 (VIII)

or

 (IX)

wherein Z' has been defined, the average value of x' may vary from about 5 to about 150 and the average value of y' may vary from 2 to about 8. Such preferred acryloxy-functional organopolysiloxanes are fluids having a viscosity between about 10 and 1000 cP at 25° C.

Similarly, the most preferred acrylamide-functional organopolysiloxanes of this invention have the structure

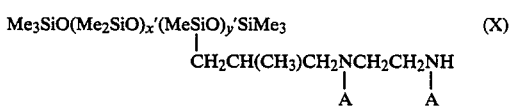 (X)

in which A is the radical

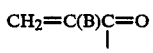

and B is hydrogen or methyl. Here the average value of x' may vary from about 5 to 100 and the average value of y' may vary from 2 to about 5. This acrylamide-functional organopolysiloxane may be prepared according to methods described by Varaprath, cited supra.

The non-reactive units (i.e., those which do not contain reactive groups X or Z) of organopolysiloxanes (i) and (ii) may be composed of any combination of siloxane units of the formulae R$_3$SiO$_{\frac{1}{2}}$, R$_2$SiO$_{2/2}$, and SiO$_{3/2}$, and SiO$_{4/2}$, bonded together by Si—O—Si bonds. Examples of suitable non-reactive siloxane units for either component (i) or (ii) are end-blocking triorganosiloxane units, such as Me$_3$SiO$_{\frac{1}{2}}$, PhMe$_2$SiO$_{\frac{1}{2}}$, CF$_3$CF$_2$CF$_2$CF$_2$CH$_2$Ch$_2$Me$_2$SiO$_{\frac{1}{2}}$, CF$_3$CH$_2$CH$_2$Me$_2$SiO$_{\frac{1}{2}}$ and Ph$_2$MeSiO$_{\frac{1}{2}}$; backbone diorganosiloxane units, such as Me$_2$SiO$_{2/2}$, PhMeSiO$_{2/2}$, CF$_3$CH$_2$CH$_2$MeSiO$_{2/2}$, Ph$_2$SiO$_{2/2}$, ClCH$_2$CH$_2$CH$_2$MeSiO$_{2/2}$ and CF$_3$CF$_2$CF$_2$CF$_2$CF$_2$CH$_2$MeSiO$_{2/2}$; and branching monoorganosiloxane units, such as MeSiO$_{3/2}$, PhSiO$_{3/2}$ and SiO$_{4/2}$. Herein, Me denotes the methyl radical and Ph denotes the phenyl radical.

In addition to the groups delineated above, components (i) and (ii) may contain small amounts of non-essential radicals such as silicon-bonded hydroxy, methoxy, ethoxy and acetoxy radicals. These radicals are usually bonded to endblocking siloxane units by design or are present on siloxane units as a residual radical arising from the particular process that was used to prepare the component. Preferably, components (i) and (ii) are free of such non-essential radicals.

To be within the scope of this invention, no organopolysiloxane molecule bears both reactive amine-functional radicals and reactive acryl-functional radicals. Preferably, no siloxane unit of the organopolysiloxanes (i) and (ii) bears more than one of said reactive groups X and Z, respectively. Furthermore, for either component (i) or component (ii), any combination of reactive and non-reactive organosiloxane units, which is within the above-mentioned constraints, may be used, provided that the convertible organopolysiloxane compositions are liquid at room temperature, i.e., they flow. The initial viscosity of the liquid mixture is not critical and may range from about 10 to about 4000 cP at 25° C. A preferred viscosity of the covertible organopolysiloxane composition to be used for any particular combination of internal material and fluid continuous phase may be determined by routine experimentation.

When components (i) and (ii) are free of —$SiO_{3/2}$ and $SiO_{4/2}$ siloxane units, and the total of all the reactive radicals in (i) and (ii) does not exceed about 10 percent of all the radicals therein, the compositions of this invention generally form elastomeric microparticles when cured. Such is the case when the preferred amine-functional organopolysiloxanes are combined with the preferred acryl-functional organopolysiloxanes of this invention. As the number of —$SiO_{3/2}$ and $SiO_{4/2}$ siloxane units and/or the percentage of reactive radicals therein are are increased, more resinous microparticles are obtained.

As will be apparent to those skilled in the art, at least one of the components, (i) or (ii), must have an average reactive functionality greater than two in order to effect a cure in the compositions of this invention. Thus, for example, if component (i) has, on average, only 2 amine groups per molecule, component (ii) must have an average acryl content of greater than 2 groups per molecule.

In order to be within the scope of the present invention, the molar ratio of the active hydrogen of the amine groups of said amine-functional organopolysiloxane (i.e., =NH) to the acryl (i.e., acryloxy, methacryloxy or acrylamide) groups of said acryl-functional organopolysiloxane should be close to stoichiometric proportion. This ratio should thus range from about 0.9 to 1.1. Preferably, this ratio should be about 0.95 to 1.05, most preferably, about 1.0.

The preferred embodiments of this invention result in elastomeric microparticles which are formed by curing the preferred convertible organopolysiloxane compositions at room temperature for a period of about 15 minutes to 48 hours. These compositions result when component (i) is selected from the siloxanes represented by formula (II) or formula (III), above, and contains up to about 10 mole percent amine-functional siloxane units. Likewise, component (ii) is selected from the siloxanes represented by either formula (VI) or formula (VII), above, and contains up to about 10 mole percent acryl-functional siloxane units. The most preferred convertible organopolysiloxane compositions of this invention result when component (i) is represented by formula (IV), above, and component (ii) is selected from formula (VIII) or formula (IX), above.

In the preferred systems, the relative contents of the respective amine and acryl groups may be varied according to well-established practice in the art order to achieve desired final properties in the cross-linked microparticles. For example, if high modulus microparticles are desired, the number of reactive groups per molecule of the respective components is increased, while if low modulus material is the object, the number of such reactive sites is reduced. In this regard, it will be evident to those skilled in the art that it is sometimes beneficial to formulate a mixture wherein one of the components (i) or (ii) has more than two reactive groups per molecule while the other component is incorporated as a blend of polymers comprised of molecules having just two reactive groups as well as molecules having more than two reactive groups, the desired stoichiometric ratio of amine groups to acryl groups being preserved. In such a case the component having just two reactive groups per molecule is said to be a "chain extender" and acts to further reduce the modulus of the resulting cured elastomer.

In addition to the components (i) and (ii), the convertible compositions of the present invention may contain inhibitors, solvents, pigments, dyes, stabilizers, extenders and plasticizers as well as other adjuvants commonly employed in the art The internal material, i.e. the material to be encapsulated by the process of this invention, may be any solid particle, liquid or gas which does not chemically react with the fluid continuous phase or the convertible organopolysiloxane composition or which does not dissolve extensively in the fluid continuous phase.

Examples of suitable internal materials for this invention include corrosion inhibitors, adhesives, catalysts, colorants, cosmetics, curing agents, deodorants, detergents, drugs, enzymes, flavors, foods, fuels, inks, insecticides, metals, medicaments, monomers, fragrances, oils, pheromones, plasticizers, propellants, solvents, solid substrates containing an absorbed active compoenent and vitamins.

When microencapsulating solid materials it is preferred to reduce the material to the desired particle size before preparing the dispersion to be cured. Liquid internal materials need no special treatment. Gaseous materials are best microencapsulated using the method for preparing discrete entities comprising dispersing the gas in the liquid organopolysiloxane compositions, as a first step.

The fluid continuous phase must be chemically unreactive with and not dissolve the convertible organopolysiloxane composition. Although it is not necessary, especially when preparing microcapsules having a dispersed internal material, it is preferred that the fluid continuous phase will not dissolve the internal material extensively.

The fluid continuous phase may be a gas, but preferably it is a liquid of suitable viscosity to permit the forming and maintaining of the dispersion.

Examples of fluids that are suitable for use as the continuous phase in the method of this invention are air, nitrogen, steam, water, mineral oil, and perfluorocarbons. Selection of a suitable match of internal material and fluid continuous phase should be made to satisfy the non-reactivity and non-solubility requirements noted above.

In a preferred embodiment of this invention the fluid continuous phase is water which contains a dispersion-stabilizing amount of a surfactant of the oil-in-water type to aid in the formation of the dispersion and to minimize agglomeration of discrete entities and microparticles during cure. Said surfactant may be the anionic type, such as salts of alkyl sulfates, salts of alkyl benzene sulfonates and salts of poly(oxyethylene)alkyl ethers, poly(oxyethylene)alkylphenol ethers, and poly(oxyethylene)alkyl esters. Preferably any surfactant that is used is free of any groups which can react with the convertible organopolysiloxane composition. The proper amount of oil-in-water type surfactant to be used may vary widely and can be determined by simple experimentation. Generally, less than 5 percent by weight, based on the weight of water, is sufficient.

In the method of this invention a dispersion consisting essentially of discrete entities, hereinafter further delineated, dispersed in a fluid continuous phase, is prepared and is cured via the Michael addition to convert the discrete entities to microparticles. Said dispersion may be prepared by any suitable method, such as stirring, homogenizing and emulsifying, which will provide a discontinuous phase of discrete entities which are maintained in the dispersed state while the dispersion is being cured.

In one embodiment of this invention, which provides microspheres, the discrete entities consist essentially of spheres, up to about 5 mm in diameter, of a liquid organopolysiloxane composition which is convertible to the solid state. These discrete entities may be prepared by dispersing the liquid organopolysiloxane composition in the continuous phase fluid using any suitable method for dispersing a liquid in an incompatible fluid. These methods are well known in the art and need not be detailed here. These discrete entities experience a curing reaction which converts them to the solid state to provide microspheres. These microspheres, either elastomeric or resinous, are useful as filler particles in various fluid compositions such as greases, sealants and adhesives and as substrate particles in chromatography columns.

In another embodiment of this invention, which provides microcapsules, the discrete entities consist essentially of sphere-like particles, up to about 5 mm in diameter, having an internal material surrounded by a convertible organopolysiloxane composition. The convertible organopolysiloxane composition is converted to the solid state thereby encapsulating the internal material and providing microcapsules. These microcapsules are useful as time release capsules, such as for the controlled release of herbicides, fertilizers and medicaments. However, the type of microcapsules that are produced by the method of this invention is determined by the manner in which the dispersion to be cured is prepared.

In a first manner for preparing the dispersion of discrete entities consisting essentially of an internal material surrounded by a convertible organopolysiloxane composition the internal material to be microencapsulated is first dissolved or dispersed in the convertible organopolysiloxane composition and the resulting solution or dispersion is thereafter dispersed in the continuous phase fluid. In this manner a major portion of microcapsules containing the internal material dissolved and/or dispersed throughout the solid organopolysiloxane is obtained after cure. When the internal material is insoluble in the liquid organopolysiloxane composition, there also may be obtained minor amounts of microcapsules containing a discrete core of internal material. To provide a maximum portion of microcapsules having a dispersed internal material, vigorous mixing of the internal material and the convertible organopolysiloxane composition should be used. In some cases it may be desired or necessary to use a suitable surfactant to achieve proper dispersion of an internal material which is insoluble in the convertible organopolysiloxane composition.

In a second manner for preparing the dispersion of discrete entities consisting essentially of an internal material surrounded by a convertible organopolysiloxane composition the internal material to be encapsulated is despersed in the continuous phase fluid and the convertible organopolysiloxane composition is simultaneously, or subsequently, codispersed therewith. In this manner a major portion of microcapsules containing the internal material localized as a discrete core in the solid organopolysiloxane is obtained after cure. There also may be obtained by this second manner minor amounts of microspheres of solid which are free of the internal material. For maximum yield of microcapsules having a discrete core of internal material it is preferred to disperse the internal material and the convertible organopolysiloxane composition simultaneously in the fluid continuous phase, using moderate mixing such as stirring, rather than homogenizing or emulsifying.

The dispersion of discrete entities in fluid continuous phase is cured until the desired degree of solidification of the convertible organopolysiloxane composition has been achieved. This is conveniently determined by visual inspection. In a preferred method, aliquots of the dispersion are periodically taken and examined under magnification. The dispersion is cured at least until the convertible organopolysiloxane is non-flowing. This is conveniently determined by placing the microparticles on a microscope slide and ascertaining the absence of organopolysiloxane film formation on the slide. Preferably the dispersion is cured until the microparticles have sufficient strength to permit isolation by standard methods such filtration and centrifugation without fragmenting the solid organopolysiloxane. Curing may be accomplished at elevated temperatures of about 50° C. to 150° C., but is preferably carried out at room temperature.

In the method of this invention the microparticles may be separated from or allowed to remain in the reaction mixture after cure, as desired. However, because of the previous nature of organopolysiloxane elastomers and resins, microcapsules containing an internal material which is soluble in the fluid continuous phase should be separated from the fluid continuous phase as soon as they are formed or shortly thereafter to minimize any undesired leaching of the internal material by the fluid continuous phase.

EXAMPLES

The following examples are presented to further illustrate the process of this invention, but are not to be construed as limiting the invention, which is delineated in the appended claims. All parts and percentages in the examples are on a weight basis unless indicated to the contrary.

EXAMPLE 1

Into a 2-liter flask, equipped with magnetic stirrer, water trap and condenser, was charged 195 grams of 3-allyloxy-1,2-propanediol, 225 grams of acetone and 480 grams of toluene. Four grams of concentrated sulfuric acid was then added to this mixture. This combination was stirred and heated to reflux, whereupon the water which formed was trapped over a 13 hour period. The reaction mixture was cooled to room temperature and neutralized with 50 grams of NaHCO$_3$. Distillation of the organic layer yielded 161 grams of a product having the formula

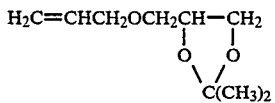

which product had a boiling point range of 57°–58° C. at 4.5 mm Hg.

EXAMPLE 2

Twenty grams of the product of Example 1 was mixed with 80 grams of an SiH-terminated siloxane having, on average, the formula H(Me$_2$)SiO(Me$_2$SiO)$_{14}$Si(Me$_2$)H wherein Me represents the methyl group. To this mixture was added 0.006 grams of a platinum catalyst which contained 4% platinum and was prepared according to the method described in Example 1 of Willing U.S. Pat. No. 3,419,593. The mixture was stirred and reaction was evidenced by a mild exotherm whereupon the temperature rose to about 70° C. Reaction was completed by heating at 70° C. for an additional 5 hours, at which point the infrared absorption due to SiH (2170 cm-1) had disappeared. The product had the average structure Z"(Me$_2$)SiO(Me$_2$SiO)$_{14}$Si(Me$_2$)Z"

wherein Z" is the group

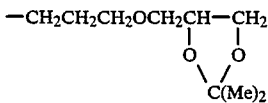

EXAMPLE 3

To a mixture of 30 grams of methyl alcohol and 3 grams of concentrated hydrochloric acid was added 98 grams of the product of Example 2. This combination was heated up to a temperature of 74° C. to remove volatiles and further stripped at 80° C./30 mm Hg for about 30 minutes. The product was cooled to room temperature and filtered to yield 83.5 grams of a viscous fluid having the average structure Z'''(Me$_2$)SiO(Me$_2$SiO)$_{14}$Si(Me$_2$)Z''' wherein Z''' is

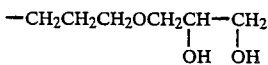

The theoretical hydroxyl content of 4% was confirmed as 4.0%±/−0.2%.

EXAMPLE 4

Into a 50-ml flask, equipped with a water trap and condenser, was charged with 12.6 grams of fluid of Example 3, 0.006 gram of hydroquinone, 0.03 gram of concentrated sulfuric acid, 18 grams of toluene and 2.5 grams of acrylic acid. This mixture was heated to reflux and all the water which formed was trapped. At this point, the reaction mixture was stripped at 50° C. and 30 mm Hg to remove volatiles. The stripped fluid was an acrylate-functional polydimethylsiloxane having the average structure Z'(Me$_2$)SiO(Me$_2$SiO)$_{14}$Si(Me$_2$)Z' wherein Z' is the group

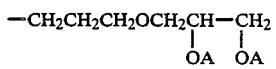

in which A is

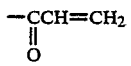

EXAMPLE 5

In an alternate preparation of the acrylate-functional polydimethylsiloxane of Example 4, 83.7 grams of a fluid prepared according to the method of Example 3, above, was mixed with 17.3 grams of acryloyl chloride and 0.02 gram of hydroquinone. This mixture was heated 135° C. for 30 minutes, cooled to 40° C. and neutralized with 3 grams of solid calcium carbonate for an additional 30 minutes. The product was filtered and stripped at 35°–40° C. 10 mm Hg for 30 minutes to yield 91.7 grams of the material having the average structure shown in Example 4.

EXAMPLE 6

Into a 100 ml flask equipped with a stirrer, thermometer and stopper, was charged 18.7 grams of an acrylate-functional polydimethylsiloxane prepared according to example 5 and 59.9 grams of a blend of cyclic dimethylsiloxanes having about three to six siloxane units. To this mixture was added about 0.02 gram of trifluoromethane sulfonic acid. The reactants were stirred and heated at 70° C. for 3 hours. The resulting fluid was neutralized with solid CaCO$_3$ (2 grams) and filtered. The resulting filtrate was stripped at 100° C./ 5 mm Hg and had the average structure Z'(Me$_2$)SiO(Me$_2$SiO)$_{98}$Si(Me$_2$)Z' wherein Z' is the group

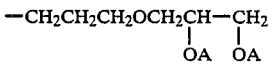

in which A is

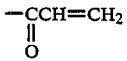

EXAMPLE 7

Dichromate quaternary salt is a sticky brown oil described as an organic dichromate complex and is utilized as a corrosion inhibitor in marine antifouling paints. This salt is sensitive to chloride ion and requires encapsulation for stablility in such systems. To 2 grams of an amine-functional siloxane having the average formula $$Me_3SiO(Me_2SiO)_{188}(MeSiO)_{10}SiMe_3$$
$$\underset{X'}{|}$$

wherein Me denotes the methyl radical, and X' represents the group $$-CH_2\underset{Me}{\overset{|}{C}}HCH_2\underset{H}{\overset{|}{N}}CH_2CH_2NH_2$$

was added 0.3 gram of the dichromate quaternary salt. To this mixture was added 1 gram of the acrylate-functional polydimethylsiloxane of Example 4. This combination was stirred with a spatula for about one minute and then added to a solution consisting of 0.03 gram of Triton (R) X-100 surfactant in 300 grams of water. Triton (R) X-100 (Rohm and Haas, Philadelphia, Pennsylvania) is described as octylphenoxypolyethoxy(10)ethanol. The mixture so formed was stirred for about 3 hours using a magnetic stirrer, after which it was vacuum filtered to yield brown-colored beads which were dry to the touch.

No dichromate quaternary salt was observed in the filtrate, indicating successful encapsulation thereof. Furthermore, the beads were washed with acetone, which solvent can solubilize the salt. After 3 such washes, there was no discoloration of the acetone, again indicating that little salt remained on the surface of the beads. This example illustrates the effective encapsulation of an opaque material.

EXAMPLE 8

A fragrance oil containing olefinic unsaturation, (46.113/E; Eurand America, Inc., Vandalia, Ohio) is described as a perfume oil having an herbal odor, a specific gravity of 1.021–1.041, a flash point of 167° C. and being slightly soluble in water. To a mixture of 1 gram of the acrylate-functional polydimethylsiloxane of Example 4 and 2 grams of the aminefunctional siloxane described in Example 7, was added 0.2 gram of the fragrance oil containing olefinic unsaturation. The mixture so formed was added to a solution consisting of 0.04 gram of Triton (R) X-100 surfactant in 300 grams of water. The combination was stirred overnight using a magnetic stirrer. The spherical beads which formed were isolated by vacuum filtration and retained the odor of the fragrance for at least 60 days. This example illustrates the effectivess of encapsulating a material containing olefinic unsaturation.

EXAMPLE 9

Acetaminophen (Mallinckrodt, Inc., St. Louis, Missouri) is described as 4-acetamidophenol, CAS No. 103-90-2. Three grams of acetaminophen was mixed with 4 grams of the aminefunctional siloxane described in Example 7 using a spatula. To this blend was added 2 grams of the acrylate-functional polydimethylsiloxane of Example 4 with further mixing. This combination was poured into a solution consisting of 3 drops of Triton (R) X-100 surfactant in 300 grams of water and mixed using a magnetic stirrer. After about 60 minutes, the product was isolated by vacuum filtration and dried in a desiccator. Under microscopic examination, the product was observed to comprise spherical beads of having a diameter of about 0.5–2 mm. When such observation was carried out using polarized light, the presence of the crystalline acetaminophen within the silicone beads was apparent.

EXAMPLE 10

One gram of Drakeol (R) 10 (Penreco, Butler, Pennsylvania) a white mineral oil having the designation U.S.P. No. 95/105 was added to a solution consisting of 3 drops of Triton (R) X-100 surfactant in 300 grams of water and the resultant suspension was stirred mechanically for about 2 minutes. To this mixture, was added a pre-blend consiting of 2 grams of the amine-functional siloxane of Example 7 and 1 gram of the acrylate-functional polydimethylsiloxane of Example 4. This combination was further stirred overnight at room temperature. When this combination was vacuum filtered to isolate the product, no oil could be detected in the filtrate. The isolated product consisted of dry, spherical beads that, when crushed under pressure, released the mineral oil.

EXAMPLE 11

Amyloglucosidase (Sigma Chemical Co., St. Louis, Missouri) is described as an enzyme derived from Rhizopus Mold which is active with respect to the conversion of starch to glucose. Five grams of an acryloxy-functional organopolysiloxane prepared according to the methods of Example 4, above, was mixed with 10 grams of an aminefunctional organopolysiloxane having the structure shown in Example 7, above. To this mixture was added 5 grams of amyloglucosidase and this combination was further mixed slowly for 2 minutes using a glass stirring rod.

The above mixture was added to a 1000 ml flask containing 500 cc water and 10 drops of Triton (R) 100. This mixture was dispersed by mixing with a mechanical paddle stirrer for 55 minutes. Solid, light brown spheres of the enzyme encapsulated in cured organopolysiloxane were then isolated by filtration, as in previous examples.

The activity of the encapsulated amyloglucosidase was determined by placing a sample thereof in a 1% starch in water solution for 10 minutes at 55° C. This resulted in rate of conversion (i.e., starch to glucose) of $1.55 \times 10^{-2}$ (mg glucose)/(mg encapsulated enzyme) (minute).

(Comparative) Example 12

The dichromate quaternary salt used in Example 7, above, was encapsulated according to the method described by Ziemelis in U.S. Pat. No. 4,370,160. In this example, the mercapto-functional silicone had the average structure $$Me_3SiO(Me_2SiO)_{113}(MeSiO)_{10}SiMe_3$$
$$\underset{CH_2CH_2CH_2SH}{|}$$

and the olefin-functional silicone had the average structure $$Me_3SiO(Me_2SiO)_{243}(MeSiO)_5SiMe_3$$
$$\underset{CH_2CH_2-}{|}$$

Each of these silicones was blended with the photoinitiator benzophenone, such that the latter compound constituted 1.5% of each respective blend. 10.0 grams of the mercaptofunctional silicone was thoroughly mixed with 20.0 grams of the olefin-functional silicone. This mixture was further mixed with 4.0 grams of the dichromate quaternary salt, using an Eppenbach Homomixer (R), and dispersed in 400 ml of water containing 0.6 gram of Triton(R) X 100. This dispersion was stirred in a reaction tube and irradiated with a UV medium pressure mercury vapor lamp placed approximately 10 mm from the tube. After one hour of irradiation, little cure was evident. The dispersion was allowed to stir overnight (without irradiation), whereupon partial cure took place. However, the particles, when isolated, were still sticky to the touch. This observation illustrates the difficulty of forming a UV-cured encapsulation system when the material to be encapsulated results in inhibition of the UV cure.

(Comparative) Example 13

The fragrance oil-containing olefinic unsaturation used in Example 8, above, was encapsulated according to the method described in Example 11, above. As in Example 11, each silicone reactant was blended with benzophenone, such that the latter compound constituted 1.5% of each respective blend. A homogeneous mixture of 8.33 grams of the mercaptofunctional silicone with 16.66 grams of the olefin-functional silicone was prepared. This mixture was added to a reaction flask containing 25 grams of the fragrance oil dispersed in 400 ml of water containing 0.4 gram of octylphenoxypolyethoxy(40)ethanol (Triton(R) 405, Rohm and Haas, Philadelphia, Pennsylvania). This dispersion was stirred in the reaction flask and irradiated with a UV medium pressure mercury vapor lamp placed approximately 10 mm from the flask. After 1 hour of irradiation, little cure was evident; the particles, when isolated, were still sticky to the touch and incompletely cured. This observation illustrates the difficulty of forming a UV-cured encapsulation system when the material to be encapsulated contains olefinic unsaturation.

We claim:

1. A process for preparing microspheres of solid organopolysiloxane, said process comprising:
   (I) preparing a dispersion of discrete entities in a fluid continuous phase by dispersing, in the continuous phase fluid, a liquid organopolysiloxane composition convertible to a solid state at room temperature by a Michael-type addition reaction, said liquid organopolysiloxane composition being insoluble in the fluid continuous phase and consisting essentially of
      (i) an organopolysiloxane having attached thereto through silicon-carbon bonds an average of at least two X groups per molecule, wherein X is a monovalent organic moiety containing at least one —NHR" radical, wherein R" is selected from the group consisting of hydrogen and alkyl radicals having 1 to 6 carbon atoms, and
      (ii) an organopolysiloxane having attached thereto through silicon-carbon bonds an average of at least two Z groups per molecule, wherein Z is a monovalent organic moiety containing at least one acryl-functional radical which is capable of reacting with said —NHR" radical, said acryl-functional radical being selected from the group consisting of acryloxy, methacryloxy and acrylamide radicals, at least one of (i) and (ii) having an average of more than two of said X groups and said Z groups, respectively, per molecule; and
   (II) curing said organopolysiloxane composition by a Michael-type addition reaction until it is converted to a solid state.

2. The process according to claim 1, wherein said organopolysiloxane (i) is selected from the group consisting of linear copolymers having the average structure

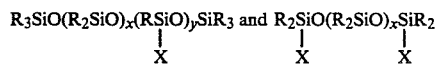

wherein R is independently selected from the group consisting of alkyl radicals having 1-6 carbon atoms, cycloaliphatic radicals, aryl radicals, monovalent halohydrocarbyl groups having 1 to 6 carbon atoms and haloaromatic groups, and in which the average value of x can vary from about zero to about 900 and the average value of y can vary from 2 to about 100; and said organopolysiloxane (ii) is selected from the group consisting of linear copolymers having the average structure

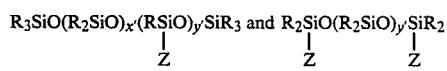

in which R has been previously defined, the average value of x' can vary from about 5 to about 150 and the average value of y' can vary from 2 to about 30.

3. The process according to claim 2, wherein said R groups of components (i) and (ii) are independently selected from the group consisting of methyl, phenyl and 3,3,3-trifluoropropyl radicals.

4. The process according to claim 3, wherein said X group is represented by the formula

in which R' is a divalent hydrocarbyl group having 3 to 6 carbon atoms, R" is selected from the group consisting of hydrogen and alkyl radicals having 1 to 6 carbon atoms and g is an integer having a value of zero to 4.

5. The process according to claim 4, wherein said Z group is represented by the formula

in which Q and Q' denote divalent hydrocarbon radicals, R"" is selected from the group consisting of hydrogen and a monovalent hydrocarbon radical and A is the group

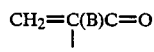

where B is selected from the group consisting of hydrogen and a methyl radical.

6. The process according to claim 5, wherein said Q group is —CH$_2$CH(CH$_3$)CH$_2$—, said Q' group is —CH$_2$CH$_2$—, said R"" group is hydrogen and said R group is methyl.

7. The process according to claim 4, wherein said Z group is represented by the formula

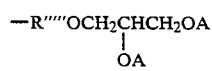

in which R''''' is a divalent hydrocarbon group having 3 to 6 carbon atoms, A is the group $$CH_2=C(B)C=O$$
| where B is selected from the group consisting of hydrogen and a methyl radical.

8. The process according to claim 7, wherein said R''''' group is trimethylene and said R group is methyl.

9. The process according to claim 1, wherein the fluid continuous phase is water comprising a dispersion-stabilizing amount of an oil-in-water surfactant.

10. A process for preparing microcapsules of an internal material localized as a core in a solid organopolysiloxane, said process comprising:
  (II) preparing a dispersion of discrete entities in a fluid continuous phase by dispersing the internal material in the continuous phase fluid and simultaneously or subsequently codispersing therewith a liquid organopolysiloxane composition convertible to a solid state at room temperature by a Michael-type addition reaction and insoluble in the fluid continuous phase, said composition consisting essentially of
    (i) an organopolysiloxane having attached thereto through silicon-carbon bonds an average of at least two X groups per molecule, wherein X is a monovalent organic moiety containing at least one —NHR'' radical, wherein R'' is selected from the group consisting of hydrogen and alkyl radicals having 1 to 6 carbon atoms, and
    (ii) an organopolysiloxane having attached thereto through silicon-carbon bonds an average of at least two Z groups per molecule, wherein Z is a monovalent organic moiety containing at least one acryl-functional radical which is capable of reacting with said —NHR'' radical, said acryl-functional radical being selected from the group consisting of acryloxy, methacryloxy and acrylamide radicals, at least one of (i) and (ii) having an average of more than two of said X groups and said Z groups, respectively, per molecule; and
  (II) curing said organopolysiloxane composition by a Michael-type addition reaction until it is converted to a solid state.

11. The process according to claim 10, wherein said organopolysiloxane (i) is selected from the group consisting of linear copolymers having the average structure $$R_3SiO(R_2SiO)_x(RSiO)_ySiR_3 \text{ and } R_2SiO(R_2SiO)_xSiR_2$$
|     |     |
X     X     X wherein R is independently selected from the group consisting of alkyl radicals having 1-6 carbon atoms, cycloaliphatic radicals, aryl radicals, monovalent halohydrocarbyl groups having 1 to 6 carbon atoms and haloaromatic groups, and in which the average value of x can vary from about zero to about 900 and the average value of y can vary from 2 to about 100; and said organopolysiloxane (ii) is selected from the group consisting of linear copolymers having the average structure $$R_3SiO(R_2SiO)_{x'}(RSiO)_{y'}SiR_3 \text{ and } R_2SiO(R_2SiO)_{y'}SiR_2$$
|     |     |
Z     Z     Z in which R has been previously defined, the average value of x' can vary from about 5 to about 150 and the average value of y' can vary from 2 to about 30.

12. The process according to claim 11, wherein said R groups of components (i) and (ii) are independently selected from the group consisting of methyl, phenyl and 3,3,3-trifluoropropyl radicals.

13. The process according to claim 12, wherein said X group is represented by the formula —R'(NHCH$_2$CH$_2$)$_g$NR''H in which R' is a divalent hydrocarbyl group having 3 to 6 carbon atoms, R'' is selected from the group consisting of hydrogen and alkyl radicals having 1 to 6 carbon atoms and g is an integer having a value of zero to 4.

14. The process according to claim 13, wherein said Z group is represented by the formula

—QNAQ'NAR'''' in which Q and Q' denote divalent hydrocarbon radicals, R'''' is selected from the group consisting of hydrogen and a monovalent hydrocarbon radical and A is the group $$CH_2=C(B)C=O$$
| where B is selected from the group consisting of hydrogen and a methyl radical.

15. The process according to claim 14, wherein said Q group is —CH$_2$CH(CH$_3$)CH$_2$—, said Q' group is —CH$_2$CH$_2$—, said R'''' group is hydrogen and said R group is methyl.

16. The process according to claim 13, wherein said Z group is represented by the formula

—R'''''OCH$_2$CHCH$_2$OA
          |
          OA in which R''''' is a divalent hydrocarbon group having 3 to 6 carbon atoms, A is the group $$CH_2=C(B)C=O$$
| where B is selected from the group consisting of hydrogen and a methyl radical.

17. The process according to claim 16, wherein said R''''' group is trimethylene and said R group is methyl.

18. The process according to claim 10, wherein the fluid continuous phase is water comprising a dispersion-stabilizing amount of an oil-in-water surfactant.

19. The process according to claim 18, wherein the internal material is selected from the group consisting of enzymes, fragrances, corrosion inhibitors, catalysts and medicaments.

20. The process according to claim 10, wherein the internal material is selected from the group consisting of enzymes, fragrances, corrosion inhibitors, catalysts and medicaments.

21. A process for preparing microcapsules of an internal material dispersed throughout a solid organopolysiloxane, said process comprising:

(I) preparing a dispersion of discrete entities in a fluid continuous phase by dispersing or dissolving the internal material in a liquid organopolysiloxane composition convertible to a solid state at room temperature by a Michael-type addition reaction and dispersing the resulting dispersion or solution in the continuous phase fluid, said organopolysiloxane composition being insoluble in the fluid continuous phase and consisting essentially of (i) an organopolysiloxane having attached thereto through silicon-carbon bonds an average of at least two X groups per molecule, wherein X is a monovalent organic moiety containing at least one —NHR" radical, wherein R" is selected from the group consisting of hydrogen and alkyl radicals having 1 to 6 carbon atoms, and (ii) an organopolysiloxane having attached thereto through silicon-carbon bonds an average of at least two Z groups per molecule, wherein Z is a monovalent organic moiety containing at least one acryl-functional radical which is capable of reacting with said —NHR" radical, said acryl-functional radical being selected from the group consisting of acryloxy, methacryloxy and acrylamide radicals, at least one of (i) and (ii) having an average of more than two of said X groups and said Z groups, respectively, per molecule; and (II) curing said organopolysiloxane composition by a Michael-type addition reaction until it is converted to a solid state.

22. The process according to claim 21, wherein said organopolysiloxane (i) is selected from the group consisting of linear copolymers having the average structure

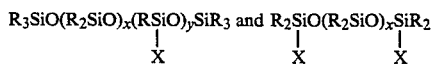

wherein R is independently selected from the group consisting of alkyl radicals having 1-6 carbon atoms, cycloaliphatic radicals, aryl radicals, monovalent halohydrocarbyl groups having 1 to 6 carbon atoms and haloaromatic groups, and in which the average value of x can vary from about zero to about 900 and the average value of y can vary from 2 to about 100; and said organopolysiloxane (ii) is selected from the group consisting of linear copolymers having the average structure

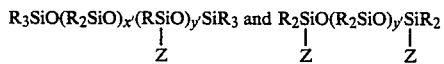

in which R has been previously defined, the average value of x' can vary from about 5 to about 150 and the average value of y' can vary from 2 to about 30.

23. The process according to claim 22, wherein said R groups of components (i) and (ii) are independently selected from the group consisting of methyl, phenyl and 3,3,3-trifluoropropyl radicals.

24. The process according to claim 23, wherein said X group is represented by the formula

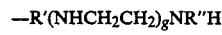

in which R' is a divalent hydrocarbyl group having 3 to 6 carbon atoms, R" is selected from the group consisting of hydrogen and alkyl radicals having 1 to 6 carbon atoms and g is an integer having a value of zero to 4.

25. The process according to claim 24, wherein said Z group is represented by the formula

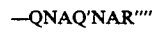

in which Q and Q' denote divalent hydrocarbon radicals, R"" is selected from the group consisting of hydrogen and a monovalent hydrocarbon radical and A is the group

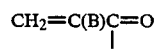

where B is selected from the group consisting of hydrogen and a methyl radical.

26. The process according to claim 25, wherein said Q group is —CH$_2$CH(CH$_3$)CH$_2$—, said Q' group is —CH$_2$CH$_2$—, said R"" group is hydrogen and said R group is methyl.

27. The process according to claim 24, wherein said Z group is represented by the formula

in which R""" is a divalent hydrocarbon group having 3 to 6 carbon atoms, A is the group

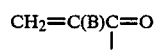

where B is selected from the group consisting of hydrogen and a methyl radical.

28. The process according to claim 27, wherein said R""" group is trimethylene and said R group is methyl.

29. The process according to claim 21, wherein the fluid continuous phase is water comprising a dispersion-stabilizing amount of an oil-in-water surfactant.

30. The process according to claim 29, wherein the internal material is selected from the group consisting of enzymes, fragrances, corrosion inhibitors, catalysts and medicaments.

31. The process according to claim 21, wherein the internal material is selected from the group consisting of enzymes, fragrances, corrosion inhibitors, catalysts and medicaments.

* * * * *